United States Patent [19]

Deem

[11] Patent Number: 5,601,538
[45] Date of Patent: Feb. 11, 1997

[54] FLOW DIRECTED CATHETER WITH HYDROPHILIC DISTAL END

[75] Inventor: Mark E. Deem, San Francisco, Calif.

[73] Assignee: Medtronic, Inc., Minneapolis, Minn.

[21] Appl. No.: 399,677

[22] Filed: Mar. 7, 1995

[51] Int. Cl.$^6$ .................................................. A61M 25/00
[52] U.S. Cl. ........................... 604/280; 604/93; 604/264; 604/265
[58] Field of Search ...................... 604/95–103, 280–283, 604/264, 265, 53

[56] References Cited

U.S. PATENT DOCUMENTS

| | | |
|---|---|---|
| 3,557,780 | 1/1971 | Sato . |
| 3,995,623 | 12/1976 | Blake . |
| 4,024,873 | 5/1977 | Antoshkiw . |
| 4,379,874 | 4/1983 | Stoy . |
| 4,563,181 | 1/1986 | Wijayarantha . |
| 4,696,304 | 9/1987 | Chin . |
| 4,771,777 | 9/1988 | Horzewski . |
| 4,774,366 | 10/1988 | Jang . |
| 4,813,934 | 5/1989 | Engelson . |
| 4,848,344 | 7/1989 | Sos . |
| 4,863,442 | 9/1989 | DeMello . |
| 4,886,506 | 12/1989 | Lovgran . |
| 4,888,364 | 12/1989 | Graiver . |
| 4,943,618 | 6/1990 | Stoy . |
| 5,061,254 | 10/1991 | Karakelle . |
| 5,091,205 | 2/1992 | Fan . |
| 5,147,370 | 9/1992 | McNamara . |
| 5,171,221 | 12/1992 | Samson . |
| 5,209,727 | 5/1993 | Radisch, Jr. . |
| 5,225,120 | 7/1993 | Graiver . |
| 5,308,342 | 5/1994 | Sepetka . |
| 5,318,032 | 6/1994 | Lonsbury . |
| 5,336,205 | 8/1994 | Zenzen et al. . |

OTHER PUBLICATIONS

"Preparation of transparent poly(vinyl alcohol) hydrogel", S. H. Hyon, W. I. Cha, Y., Ikada. *Polymer Bulletin* 22, 119–122 (1989). Research Center for Medical Polyers and Biomaterials, Kyoto University, Sakyoku, Kyoto, Japan.

*Primary Examiner*—Randall L. Green
*Assistant Examiner*—Perry E. Van Over
*Attorney, Agent, or Firm*—Townsend and Townsend and Crew LLP

[57] ABSTRACT

A flow directed catheter (2) includes a hollow catheter body (4) having a distal section (16) constructed of a hydrophilic material. The hydrophilic distal section, typically a hydrogel, has an equilibrium water content of about 80% water by mass when hydrated. The hydrophilic distal section is soft and supple but substantially inelastic and tough enough to permit use of guide wires to help direct the catheter through difficult areas (27) and also allow a wide range of therapeutic agents to be delivered to the target site (32, 34, 36). Both the inside and outside surfaces of the catheter body can be made lubricious by surface modification or by application of a secondary, lubricious coating.

22 Claims, 3 Drawing Sheets

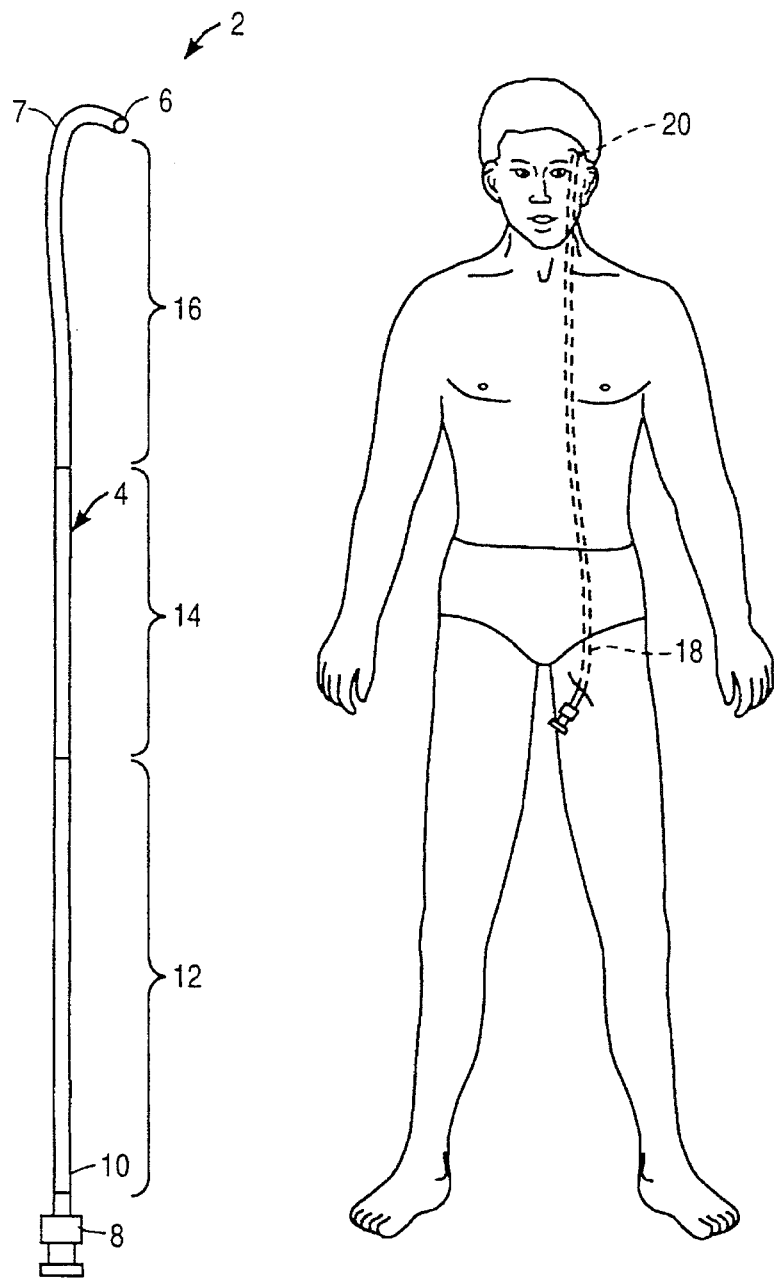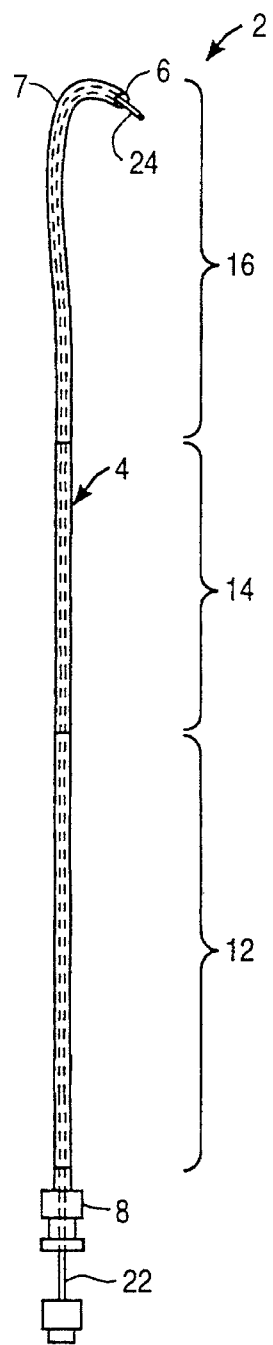
FIG. 1  FIG. 2  FIG. 3

FLOW DIRECTED CATHETER WITH HYDROPHILIC DISTAL END

BACKGROUND OF THE INVENTION

Flow directed catheters are designed so that the flow of blood through an artery directs the catheter tip along the arterial flow path and to the target site. One type of flow directed catheter uses an enlarged balloon or cup-shaped end to create a partial obstruction causing the blood flow to pull the tip of the catheter in the direction of the blood flow. See, for example, U.S. Pat. Nos. 3,995,623 to Blake et al. and 4,024,873 to Antoshkiw et al.

Another type of flow directed catheter has a very flexible distal end which is designed to be carried along by the blood flow instead of by partially blocking the artery. One of this type is manufactured by Balt S. A. of France under the trademark Magic; it is made of a hydrophobic material with a relatively stiff proximal section, a moderately flexible midsection and a quite flexible distal section. While this catheter has enjoyed some success, it has several shortcomings. The material from which the distal section is made is quite stretchable, elongates readily and has a relatively low bursting strength. This can be a problem since if a portion of the distal section breaks off from the remainder of the catheter, the broken-off portion could be left inside the vessel to cause further damage. The inside diameter of the distal section is quite small and is often not usable with a guide wire. If a guide wire is used the guide wire tends to pull on and stretch the distal section and damage the floppy tip; a guidewire could also puncture the wall of the distal section as well. These problems are due to the material from which the distal end is made. The material dictates that in order to get the desired suppleness, the distal section must have a small diameter, such as an outside diameter of 0.025 inch (0.64 mm or 2 French) and in inside diameter of 0.015 inch (0.38 mm). The small inside diameter limits the compatibility of therapies. For example, it is quite difficult, if not impossible, to inject occlusion devices such as polyvinyl alcohol (PVA) particles, metal coils, gelfoam or silk sutures with such small diameter catheters.

Another prior art flow directed catheter is manufactured by Target Therapeutics of Fremont, Calif. and is sold under the trademark Zephyr. It is intended to be used with a wire or mandrel which allows the stiffness of the midsection to be varied. The Zephyr has a lubricious, hydrophilic coating on its outside surface to aid passage of the catheter through the guiding catheters and vessels. A problem with this catheter is that it suffers from the similar limitations of the Magic catheter due to its small diameter. Also, this catheter is too stiff to access distant vascular structures. See U.S. Pat. No. 5,336,205 for Flow Directed Catheter.

SUMMARY OF THE INVENTION

The present invention is directed to a flow directed catheter in which at least the distal section is hydrophilic and is sufficiently buoyant, soft, supple and pliant to be carried along by the bloodstream. The material from which the distal section is made is substantially inelastic and has relatively high bursting strength. The hydrophilic nature of the catheter causes the distal end of the catheter to in effect become a part of the bloodstream due to its high water content. This causes the distal end of the catheter to be carried along by the bloodstream quite effectively.

The hydrophilic material, preferably a structural hydrogel, of the distal section has an equilibrium water content of about 50% to 90% water by weight, about 80% water by weight in one preferred embodiment, when hydrated. The hydrophilic distal section is large enough in diameter, having an inside diameter of about 0.010 in (0.25 mm) to 0.040 (1.0 mm) and preferably about 0.020 (0.51 mm) in one preferred embodiment, to permit the use of guide wires to help direct the catheter through difficult areas and also allow a wide range of therapeutic agents to be delivered to the target site.

A primary aspect of the invention is the recognition that a structural hydrophilic material could be used for at least the distal end of a flow directed catheter, rather than simply coating a hydrophobic material with a lubricious, hydrophilic material as is conventional. This recognition led to several advantages including better flow properties because the hydrophilic material becomes, in effect, part of the bloodstream and therefore is carried along better by the bloodstream. Instead of displacing blood and floating along with the bloodstream, as do the prior art catheters, the present invention absorbs water and effectively flows along as a part of the bloodstream. Also, the hydrophilic material permits a larger diameter catheter to be used when compared with the prior art catheters; prior art catheters are required to be relatively small in mass and size or else they will not flow with the bloodstream. With the present invention, a large part of the mass of the distal end of the catheter is water; this permits a larger catheter to be used and still be carried along by the bloodstream because of a lower solids density and the softness and suppleness of the material. The larger diameter and toughness of the material permits a wider range of therapeutic treatments while also promoting the delivery of the therapeutics deeper into the vascular region than is possible with conventional flow-directed catheters.

Another aspect of the invention is the provision of hydrophilic proximal section, a hydrophilic midsection and a hydrophilic distal section. Each hydrophilic section preferably has a different water content when fully hydrated so that the proximal section is stiffer than the midsection and the midsection is stiffer than the distal section. In addition, the inside and outside surfaces of the catheter are preferably lubricious. This can be achieved by surface modification of the hydrophilic material, application of a secondary coating, or the lubricious properties of the tubing itself.

A further aspect of the invention relates to the method by which the catheter body is made to have hydrophilic sections with different water contents. This is preferably achieved by extruding the catheter body at the highest water content of the intended final catheter. Sections of the body to be made stiffer, and thus having a lower water content when hydrated, can be heated to reduce the amount of water which can be absorbed upon hydration. This typically involves heating the proximal section to one degree and the midsection to a lower degree so the resulting catheter body, when hydrated, is stiffest at its proximal section and least stiff at its distal section.

Hydrophilic materials swell on hydration according to the amount of water they absorb. To accommodate this, the outside diameters of the sections of the catheter body before hydration are sized differently so that when hydrated the catheter body has a generally constant outside diameter. That is, before hydration the proximal end, which is typically the stiffest section, will have the largest outside diameter while the distal section, typically the least stiff, will have the smallest diameter.

Other features and advantages will appear from the following description in which the preferred embodiment has been set forth in detail in conjunction with the accompanying drawing.

BRIEF DESCRIPTION OF THE DRAWINGS

FIG. 1 is an overall view of a hydrophilic flow directed catheter made according to the invention;

FIG. 2 illustrates a guide catheter inserted into a patient;

FIG. 3 illustrates the placement of an insertion mandrel within the catheter of FIG. 1;

DESCRIPTION OF THE PREFERRED EMBODIMENT

Figure 4:
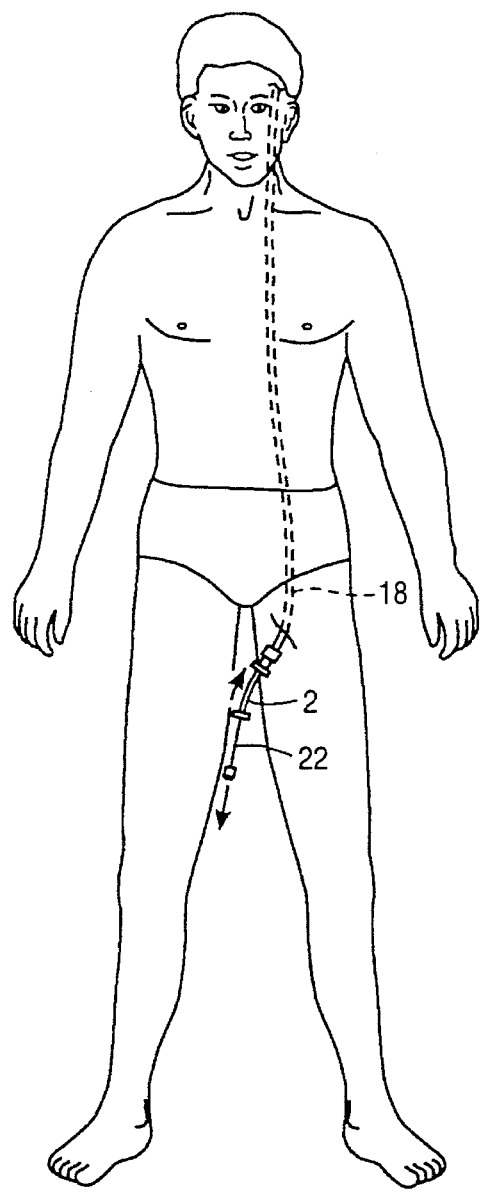
FIG. 4 shows the placement of the combination catheter and mandrel of FIG. 3 into the patient through the guide catheter of FIG. 2.
Figure 5:
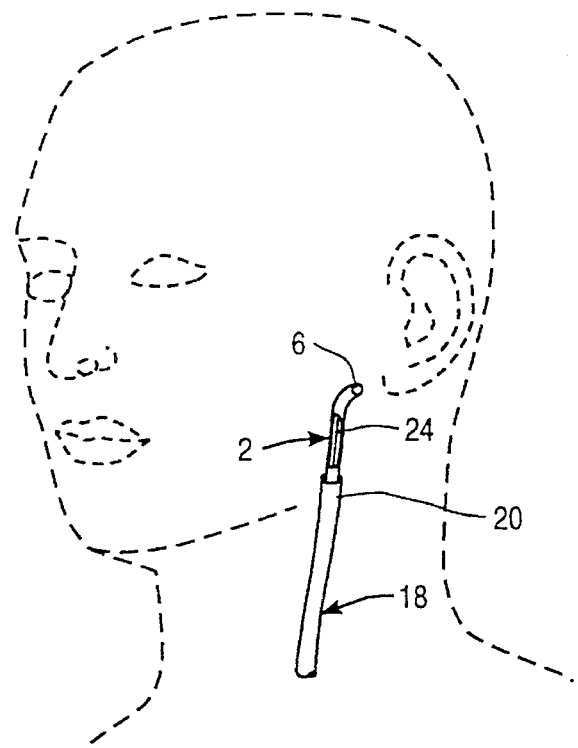
FIG. 5 is an enlarged view of the distal end of the guide catheter of FIG. 4 showing the position of the tip of the flow directed catheter just prior to the withdrawal of the insertion mandrel.

FIG. 1 illustrates a hydrophilic flow directed catheter 2 having a body 4 with an open tip 6 at the distal end 7 of body 4 and a fitting 8 at the proximal end 10 of body 4. In the preferred embodiment, body 4 is made of a hydrogel material. Body 4 preferably has lubricious outer and inner surfaces. The lubricious surfaces can be made through surface modification or application of a secondary coating. One hydrogel material, a modified polyacrylonitryl, made by Hymedix of Dayton, N.J. as Hypan can be made lubricious by modification of its surface characteristics, such as through a chemical etch. Modified polyvinyl alcohol (PVA) is a structural hydrogel which is extremely lubricous if processed to a smooth surface finish. This can be accomplished by careful extrusion of the tubing, through post processing by centerless grinding or the application of a lubricious coating to the inside and outside surfaces of the tubing. Various hydrogel materials are disclosed in U.S. Pat. Nos. 4,379,874; 4,943,618; 4,838,364; and 5,225,120. The preparation of PVA hydrogel is discussed in Polymer Bulletin 22, 119–122, Preparation of Transparent poly (vinyl alcohol) hydrogel, by Hyon, Cha, Ikada published Jul. 7, 1989. The disclosures of these patents and publication are incorporated by reference.

Catheter 2, in one preferred embodiment, is designed to treat target sites within the brain by introduction of the catheter into the vascular system through the femoral artery in the leg. Catheter 2 is about 59 inches (150 cm) long and has an inside diameter of about 0.020 in (0.51 mm) and an outside diameter of about 0.028 in (0.71 mm) after hydration. In this embodiment, body 4 includes a proximal section 12, a midsection 14 and a distal section 16. Proximal section 12 is about 43.3 inches (110 cm) long; midsection 14 is about 10 inches (25 cm) long; distal section 16 is about 6 in (15 cm) long. Other diameters and lengths can be used according to the type of therapy, the patient and the distance between the introduction site and the therapy target site.

Proximal section 12 is the stiffest of the three sections while distal section 16 is the least stiff when hydrated. When hydrated, distal section 16 is extremely supple and soft and yet mechanically strong. Distal section 16 is made of a hydrogel whose equilibrium water content is in the range of 50–90%, and preferably about 80% water by weight. By absorbing so much of its total mass from the surrounding fluid environment, transport of catheter 2 is facilitated. The large water content and extreme suppleness of the material allow larger diameter tubing to be used. This increases the therapeutic options as will be discussed below. Larger inside diameters also allow the use of insertion mandrels as well as guide wires to direct the direction of the tip 6 of body 4 in difficult anatomy. The extreme suppleness of the material causes little or no trauma to arterial intima, reducing possibility of damage and vasospasm, which reduces patient risk and increases chances of procedure success.

Midsection 14 is preferably made of a higher modulus material upon hydration so that the hydrogel material has an equilibrium water content in the range of about 10–80% when hydrated, and preferably about 60% water by weight. Proximal section 12 is preferably made of hydrogel material whose equilibrium water content is in the range of 0–70%, preferably about 35% water by weight when hydrated.

In a preferred embodiment, the entire catheter body 4 is made from a single piece of extruded modified PVA tubing. The tubing is extruded at the highest water content of the intended final body 4, in this case, 50–90% by weight water, preferably about 80%. Proximal section 12 is then heated to reduce the amount of water which can be absorbed during subsequent hydrations. This has the effect to lessen the equilibrium water content of the tubing to about 0–70% water by weight, preferably about 35%. Midsection 14 is heated to a lower degree than proximal section 12, modifying body 4 so that the equilibrium water content is about 10–80% water by weight, preferably about 60%. These steps, lowering the equilibrium water content, have the effect of creating three different stiffness zones within a single piece of tubing without the need for bonding separate pieces together. The length and/or number of these different stiffness zones can be changed at will by modifying which sections are heated and to what degree.

A property of hydrophilic materials is that they will swell upon hydration, increasing their size when exposed to an aqueous environment. The higher the equilibrium water content of the material, the greater the dimensional change. An effect of lessening the equilibrium water content of different sections of body 4 as described above is to decrease the amount that body 4 will swell upon hydration. If a piece of tubing of continuous diameter were processed as described above, when hydrated it would taper in diameter from section to section, with the proximal section (lowest water content, and stiffest) being smallest, and the distal section (highest water content, and softest) being the largest. To overcome this usually undesirable taper, the diameter of body 4 can be modified through centerless grinding, or other means, so that when dry, proximal (stiffest) section 12 has the largest diameter and distal (softest) section 16 has the smallest diameter. When exposed to an aqueous environment, body 4 will absorb water in differing amounts so that distal end 7 will swell the most, proximal end 10 the least, and the entire body 4, when hydrated will have a consistent diameter.

In an alternate embodiment, tubing made by Hymedix of Dayton, N.J. as HYPAN is extruded at its lowest water content, and then modified in various segments as described above through chemical treatment (rather than heating).

Body 4 is made radiopaque through the addition of an opacifying agent, such as barium sulfate, to the base resin from which the body is made. Alternatively, one or more radiopaque marker bands can be used adjacent tip 6 instead of making the entire body radiopaque. As shown in FIG. 1, tip 6 can be bent into a curve either at the time of manufacture or by the physician, as is conventional.

The method of use of catheter 2 will now be described with reference to FIGS. 2–10. Body 4 is first hydrated by injecting saline into the interior of body 4 and placing the entire catheter 2 in a tray of sterile water. A guide catheter 18, see FIG. 2, is placed into the femoral artery of the patient, through descending aorta, aortic arch and common cardioid arteries and the tip 20 of guide catheter 18 is located in the artery of treatment, often in the patient's head.

FIG. 3 illustrates the placement of an insertion mandrel 22 into the interior of flow directed catheter 2 until the tip 24 of mandrel 22 exits tip 6 of body 4. The combination of FIG. 3 is then inserted into the patient through guide catheter 18 as suggested in FIG. 4 until tip 6 of catheter 2 reaches tip 20 of guide catheter 18.

Figure 6:
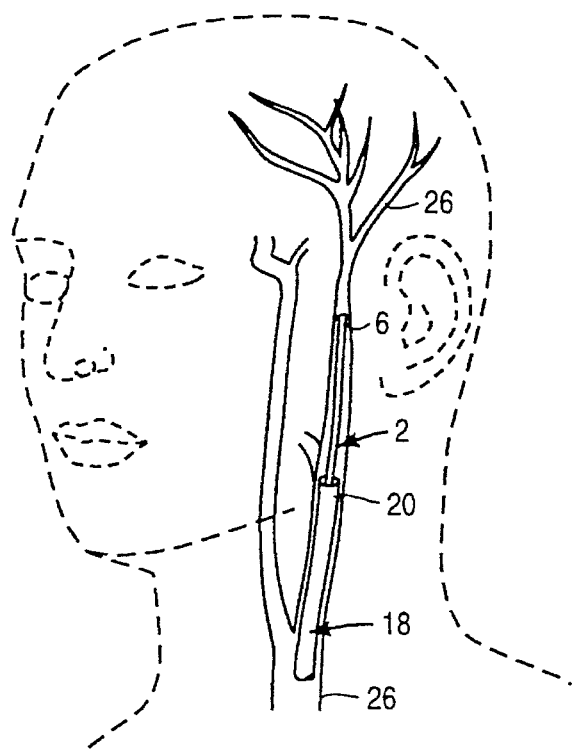
FIG. 6 illustrates movement of the flow directed catheter through an artery towards a location of treatment.
Figure 7:
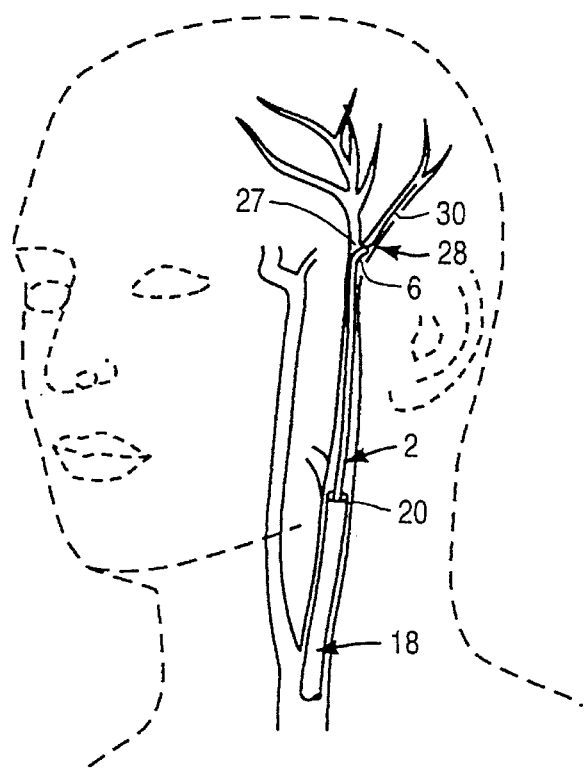
FIG. 7 illustrates the use of a guide wire to aid guiding the flow directed catheter at a difficult junction.

As tip 6 of body 4 of flow directed catheter 2 exits tip 20 of guide catheter 18, tip 24 of mandrel 22 is withdrawn so that only body 4 of flow directed catheter 2 enters artery 26 as shown in FIG. 6. Tip 6 of body 4 of flow directed catheter 2 is advanced along artery 26 by the physician manipulating the flow directed catheter tip 6 forward, with or without mandrel 22 in place, thus assisting the movement of distal section 16 of body 4 along by the blood flow in artery 26. If, as shown in FIG. 7, tip 6 of catheter 2 reaches a difficult junction 27 of an arterial tree 28, a guidewire 30 can be introduced through catheter 2 so as to negotiate junction 27 of arterial tree 28. After tip 6 of body 4 of flow directed catheter 2 is moving down the correct arterial branch, guidewire 30 can be withdrawn to permit catheter 2 to resume its flow directed state.

Figure 8:
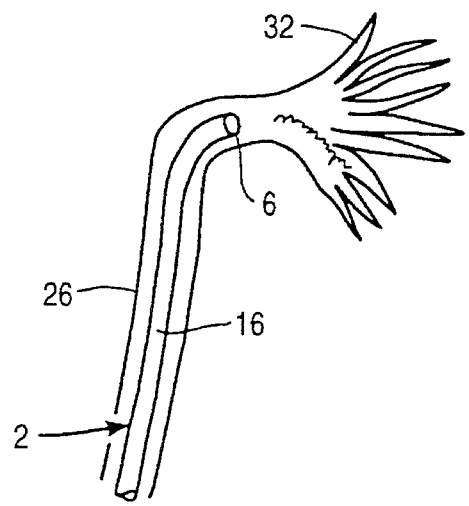
FIGS. 8, 9 and 10 illustrate delivery therapies for arteriovenous malformations (AVMs), an aneurism and a tumor, respectively.
Figure 9:
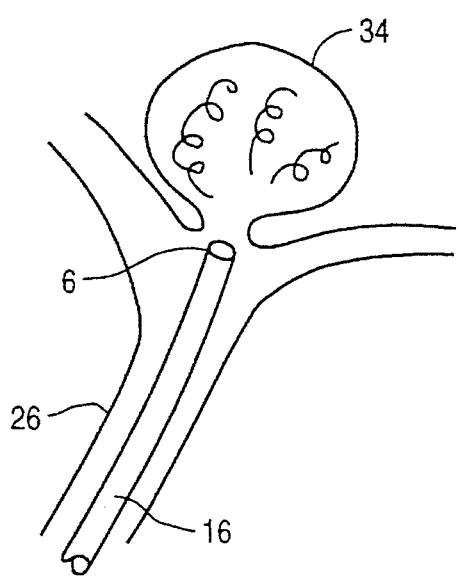
Figure 10:
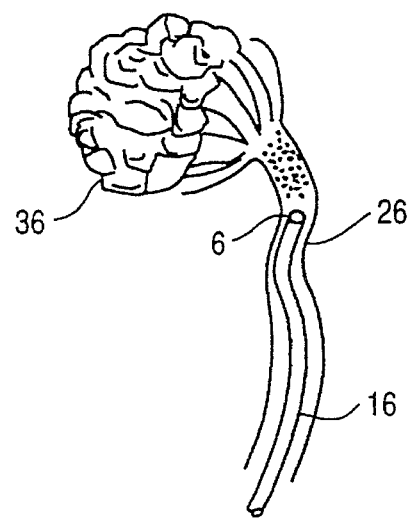

FIGS. 8–10 illustrate the delivery of therapy in three different situations with tip 6 at the target site. In FIG. 8 arteriovenous malformation (AVM) 32 is shown with tip 6 adjacent AVM. Therapies, such as those involving use of tissue adhesives, PVA (embolic particles) or coils can be provided to AVM 32 through tip 6. In FIG. 9, an aneurism 34 is shown prior to the delivery of coils, Gugliami Detachable Coils (GDC), or detachable balloons through tip 6. FIG. 10 illustrates a tumor 36 with tip 6 adjacent the tumor so as to direct therapeutic agents, such as embolic particles, tissue adhesives, or coils, to the tumor. Other therapies can also be carried out.

Modification and variation can be made to the disclosed embodiment without departing from the subject of the invention as defined in the following claims. While in the preferred embodiment body 4 is made of hydrogel material having different stiffnesses, the entire catheter body 4 could be made from a low modulus, supple, high water content material; such a catheter body could be stiffened for manipulation into the arterial pathway using an appropriate stiffening mandrel within the flow directed catheter. If desired, only distal section 16 could be made of a hydrogel material, with one or both of proximal section 12 and midsection 14 being made of less expensive, non-hydrogel material, such as plastic or stainless steel tubing. In some cases, tip 6 could be enlarged to flare out into an olive or bell shape to aid transport via the blood flow.

What is claimed is:

1. A flow directed catheter comprising:
   a hollow catheter body having a proximal section and a distal section;
   the distal section of the catheter body constructed of a structural hydrophilic material, whereby the hydrated distal section is supple and flows with blood flow as a part of the blood flow.

2. The catheter according to claim 1 wherein the distal section has an equilibrium water content of about 50% to 90% water by weight when hydrated.

3. The catheter according to claim 1 where the catheter body includes a midsection between the proximal and distal sections.

4. The catheter according to claim 3 wherein the midsection is made of a hydrophilic material.

5. The catheter according to claim 3 wherein the midsection is made of a hydrophilic material having an equilibrium water content of about 10% to 80% water by weight when hydrated.

6. The catheter according to claim 5 wherein the midsection has a lower equilibrium water content than the distal section.

7. The catheter according to claim 1 wherein the entire catheter body is made of a hydrophilic material.

8. The catheter according to claim 7 wherein the catheter body includes a midsection between the proximal and distal sections, and wherein the proximal section, midsection and distal section have equilibrium water contents of about 0 to 70%, 10 to 80% and 50 to 90% water by weight when hydrated, respectively.

9. The catheter of claim 8 wherein the proximal section, midsection and distal section have equilibrium water contents of about 35%, 60% and 80% by weight when hydrated, respectively.

10. The catheter according to claim 1 wherein the distal section has a curved tip.

11. The catheter according to claim 1 wherein at least a portion of the body is radiopaque.

12. The catheter according to claim 1 wherein the body has interior and exterior surfaces.

13. The catheter according to claim 12 wherein said exterior surface is a lubricious surface.

14. The catheter according to claim 13 wherein said exterior lubricious surface includes a lubricious surface coating.

15. The catheter according to claim 14 wherein said lubricious surface coating is a lubricious hydrogel surface coating.

16. The catheter according to claim 1 wherein the distal portion is made of a hydrogel material.

17. The catheter according to claim 1 wherein the body is made of a hydrogel material.

18. The catheter according to claim 1 wherein the distal section has an outside diameter of about 0.015 to 0.045" and an inside diameter of about 0.010 to 0.040".

19. The catheter according to claim 1 wherein the distal section has a wall with a wall thickness of about 0.002 to 0.010".

20. The catheter according to claim 1 wherein the distal section is made from a soft, supple but substantially inelastic material.

21. The catheter according to claim 1 wherein the catheter body is a one-piece tubular member.

22. A flow directed catheter comprising:
   a hollow catheter body made of a hydrophilic material and having a proximal section, a midsection and a distal section, at least a portion of the body being radiopaque;
   the body having lubricious interior and exterior surfaces; and
   the proximal section having an equilibrium water content of about 0 to 70% water by mass when hydrated, the midsection having an equilibrium water content of about 10 to 80% water by mass when hydrated and the distal section having an equilibrium water content of about 50 to 90% water by mass when hydrated, whereby the hydrated distal section is supple and flows with blood flow as a part of the blood flow.

* * * * *